United States Patent [19]

Fradera

[11] Patent Number: 4,790,753

[45] Date of Patent: Dec. 13, 1988

[54] SCREW FOR DENTAL IMPLANTS

[76] Inventor: Alejandro P. Fradera, 42, calle Angli, 08017 Barcelona, Spain

[21] Appl. No.: 152,023

[22] Filed: Feb. 3, 1988

[30] Foreign Application Priority Data

Feb. 13, 1987 [ES] Spain .................................... 00360

[51] Int. Cl.⁴ ............................................. A61C 8/00
[52] U.S. Cl. ................................................. 433/174
[58] Field of Search ................................ 433/173, 174

[56] References Cited

U.S. PATENT DOCUMENTS 2,112,007 3/1938 Adams ............................... 433/174

FOREIGN PATENT DOCUMENTS 2063680 11/1979 United Kingdom ............... 433/174

Primary Examiner—Robert Peshock
Attorney, Agent, or Firm—Michael J. Striker

[57] ABSTRACT

A screw for dental implants formed by a single main body of metal, has at the tapered bottom end thereof a central cavity extending axially up to a certain relatively small depth. The tapered bottom end merges into a long cylindrical portion provided along the whole length thereof with an outer screwthread and connected with a frustoconical portion followed by a base-column having a low height and a polygonal cross section forming the upper end of the screw. A relatively deep axial bore with a portion provided with an internal screwthread is formed in the upper end of the screw. The screwhead or starts at close to the edge of the outlet orifice and extends over the major portion of the length thereof. A non-threaded end portion terminates in the blind bottom of the said bore.

8 Claims, 1 Drawing Sheet

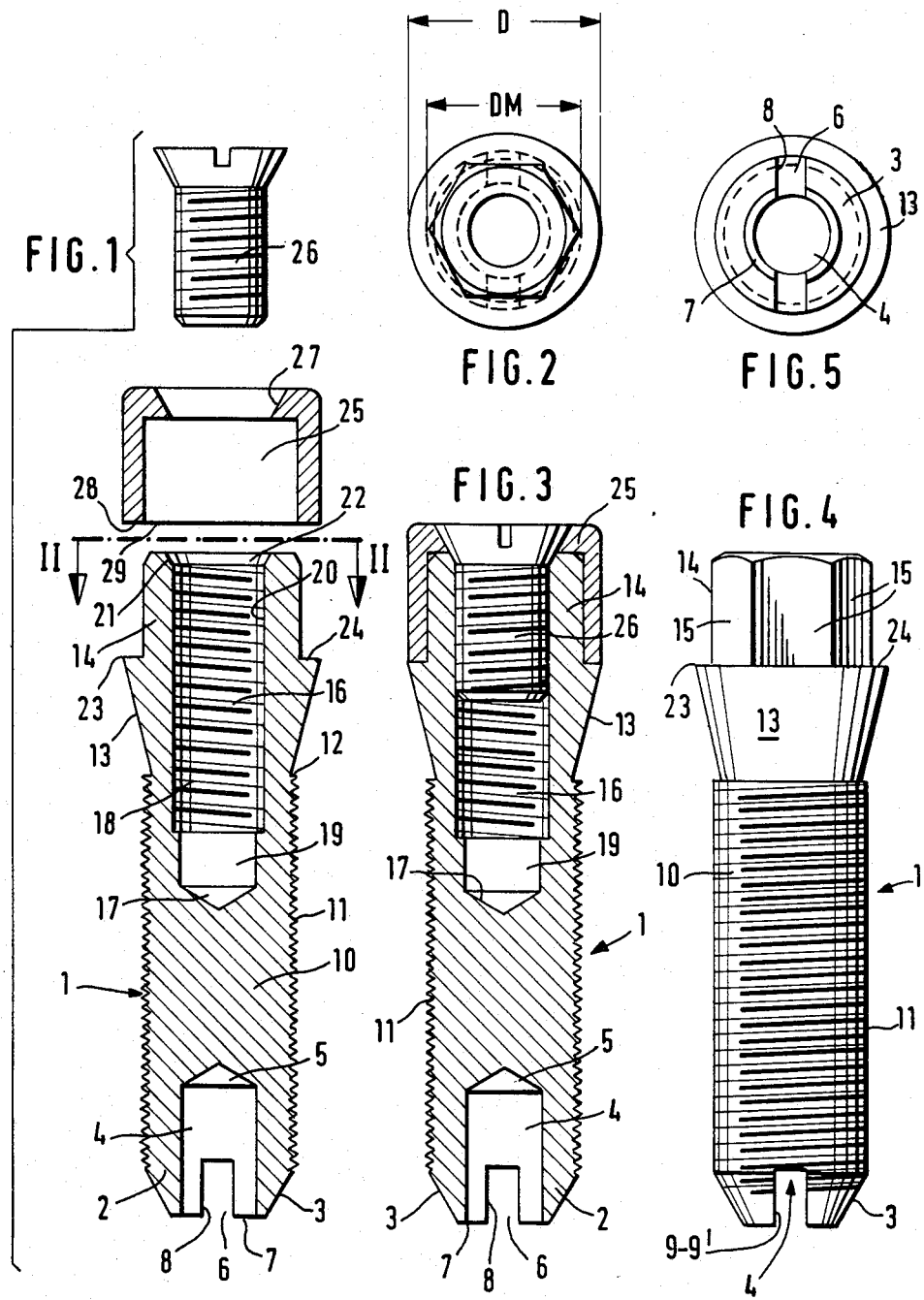

SCREW FOR DENTAL IMPLANTS

BACKGROUND OF THE INVENTION

The present invention relates to a screw for dental implants. This screw is of the type used in certain dental surgery techniques and is normally anchored in the maxillary bones and serves as a basis for holding the dental prostheses fitted subsequently. In other words, in the majority of surgical techniques for the fitting of dental prostheses, these screws are basic elements for the firm fitting of the artificial pieces replacing the diseased, faulty or deficient natural pieces.

As stated above, for several years dental surgery techniques have been known for allowing the fitting of dental prostheses by fixation or holding to anchoring members previously inserted in the bone tissue of the upper and lower maxillary bones or jawbones.

As disclosed in the German patent No. P 30 34 086.4-35, the anchoring device for the dental implant is a prismatic body which is hard to fit and which, because of its geometrical form, does not ensure a sufficiently high degree of firmness. Furthermore, there are certain difficulties for fitting this anchorage in the maxillary bone due precisely to its longer axis which is to be placed transverse relative to the axis of the dental piece.

Spanish utility model No. 272,292 discloses a screw for dental implants, the main body of which is smooth at the bottom end thereof, providing for the possibility of rotation and consequently hindering the integration of the constituent material thereof in the bone. Also, the screw disclosed in the above embodiment has the upper end thereof void of external reliefs for facilitating attachment and holding of the dental prosthesis.

Spanish utility model No. 279,140 describes an anchoring element for dental implants, similar to a screw, which comprises two separate parts and which also requires the additional use of O-rings to provide a firm attachment of the dental prosthesis.

All these embodiments and the others also known and generally used up to date may, in general terms, be included in two classes: (a) they have a simple geometrical form having the drawback of not allowing comfortable effective manageability during the implantation operations and, furthermore, they do not ensure a high degree of firm permanence in their location; and, (b) they have a complex structure, generally adapted to ensure good anchorage of both the screw in the maxillary bone and of the prosthesis to the screw itself, but they require a difficult, long, delicate assembly operation, precisely because of the complex forms and structures thereof.

Relatively low security levels of these known screws frequently lead the dental surgeons to allow a very extended period of time to elapse between the implantation of the anchoring screw and the subsequent fitting of the dental prosthesis. On many occasions this period is four, six and may even reach eight months.

SUMMARY OF THE INVENTION

It is an object of this invention to provide an improved screw for dental implants.

This and other objects of the invention are attained by a screw which is formed by a single main body and is formed to allow comfortable easy fitting, and to ensure perfect anchorage by intimate integration of said main body in the bone tissue.

Naturally the material from which the screw of the invention is made has biocompatible properties. The screw is made preferably integrally of titanium, because it is a material which guarantees a completely adequate behaviour for the purpose of the mission that this dental surgical element has to fulfil.

Other advantages derived from the new features of the screw for dental implants according to the invention are ease of use by specialists and the great adaptability to the physiological structure of this part of the human body, which allows the dental implant to be fitted within a relatively short time after placing of the screw in its location in the corresponding maxillary bone.

The screw for dental implants according to the invention is characterized in that it is formed by a single main metallic, preferably titanium, body having at the tapered lower end thereof a central cavity extending axially to a relatively small depth, said tapered lower end merging into a long cylindrical portion provided along the whole length thereof with an external screwthread connected with a frustoconical portion. There is formed between both said portions, namely the cylindrical portion and frustoconical portion, a connecting neck precisely up to which said screwthread extends, the frustoconical portion being followed by a base column of low height, having a polygonal, preferably square or hexagonal cross section, forming the upper end of the screw, and being provided, furthermore, at said upper end with an axial bore penetrating in depth approximately the half of the overall length of the screw, and in which there is a portion provided with an internal screw thread which starting at or close to the edge of the outlet orifice extends over the major portion of the length thereof A non-threaded end portion terminates in the blind bottom of the said bore.

This screw for dental implants of the invention has a very compact and functional general structure. Outstanding on the one hand, is the polygonal, preferably hexagonal form of the base column, allowing the use of auxiliary instruments of this facetted surface for aiding in the insertion of the screw in the cavity prepared in the mass of the corresponding maxillary bone.

Of course the upper axial bore is for receiving, by screwing in the corresponding anchoring stud or anchoring screw provided for such purpose in the dental prosthesis as such.

With respect to the cavity at the lower end of the screw of the invention, it performs the function of ensuring firmness of anchorage and immobility in all directions of the screw on receiving therein the growing bone tissue which forms a very compact whole.

The screw of the invention is also characterized in that the longer diagonal of the polygonal form of the said base column is shorter than the diameter of the upper circular edge of the frustoconical portion on which it is seated, such that it is completely inscribed therein, leaving free on the upper surface of said frustoconical portion a narrow annular surface.

The screw for dental implants according to the invention is further characterized in that it comprises a removable cap fitted on the base column, covering it integrally and which is held by a central retaining screw screwed in the said upper axial bore of the body of the screw for dental implants.

This base column forms the portion projecting above the level of the bone and part or whole of the frustoconical portion may also project outwards. It will be understood that the growth of the gum in the majority of cases covers all these outwardly projecting portions which, furthermore, are also covered by the covering structure of the dental prosthesis to be fitted thereafter.

It should also be pointed out that when the cap is in the fitted position, that is, covering the base column, it is also fitted to the upper surface of the frustoconical portion, the edge of the orifice thereof being seated on the free narrow annular surface.

The purpose of the cap is also very important. As is known, just after a screw or similar item has been inserted in the maxillary bone, a certain length of time, depending on the features of the process followed, must be allowed to elapse before fitting the dental prosthesis. During this waiting time, the fleshy tissue of the gum grows and consequently in a short time it would penetrate in or cover the axial bore which extends from the upper end of the single body of the screw, making it unusable or hindering its subsequent use. To avoid this drawback, the cap protects the whole of the upper portion of the screw, that is both the upper surface of the frustroconical portion and the polygonal base column, as well as the access to the axial bore.

A further unique feature of the screw according to the invention is that the central cavity at the lower end thereof is provided in the free edge of the outlet orifice with a diametral transverse cut forming two notches in mutually opposite positions.

The purpose of assuring anchorage and immobility of the central cavity is increased in effectiveness by the additional utility provided by the said cut. Said cut forms two notches which provide a sort of nipper particularly appropriate for forming a more intimate bond with the bone tissue when this extends by natural growth.

BRIEF DESCRIPTION OF THE DRAWINGS

FIG. 1 is an exploded, longitudinal cross section view of the components of the screw of the invention, arranged in straight alignment;

FIG. 2 is a top plan view of the screw;

FIG. 3 is a similar view to that of FIG. 1, wherein the component parts of the screw are assembled together;

FIG. 4 is an elevation view of the screw of the invention; and

FIG. 5 is a plan view of the lower end of the screw.

DETAILED DESCRIPTION OF THE PREFERRED EMBODIMENT

The screw for dental implants of the invention, shown as an example in the drawings is formed by the single main body 1. The material chosen for this screw is titanium, since it is one of the materials offering the best results from the medical point of view. Namely, it is the one out of the several materials experimented up to date offering less cases of rejection and which becomes best integrated into the bone tissue.

The main body 1 is provided at the bottom end 2 thereof, with a tapering tip 3, and in the lower end 2 there is a central cavity 4 extending a relatively small depth into the main body. It may be seen in FIGS. 1 and 3 that the bottom 5 of cavity 4 is blind.

The central cavity 4 defines an outlet orifice 6 formed at the free edge 7 of circular shape and defined by a diametral transverse cut 8 forming two respective notches 9-9', each located on one side of the said edge 7 as shown in FIGS. 4 and 5.

These structural elements of the screw according to the invention guarantee a firmness of anchorage of the screw in the maxillary bone receiving it, since, on the one hand, the screw ensures a more effective holding right from the time when the screw was screwed into the orifice formed in the bone for such purpose, thanks to the binding effect against the bony mass ocurring along the sharp edges formed along the notches 9-9'. Bearing in mind the natural direction of unscrewing of the screw, it is understood that of the four edges formed by the two notches 9-9', two of them are those which most effectively operate in said direction. And, furthermore, said notches are very effective during the time of adaptation of the screw to the bone, since they allow the bone tissue growing after the traumatism suffered when first drilling the hole, to expand to a certain extent in the free space defined thereby, providing an intimate, very fast bond. Furthermore, the central cavity 4 allows the bony residue caused and broken away during the surgical fitting of the screw to collect therein, thereby preventing it from hindering an adequate fit.

The single main body 1 is provided with an intermediate portion which is the one of greatest length of the whole item, being identified as a cylindrical portion 10 having all along the outer surface thereof a screw thread 11. Said cylindrical portion 10 terminates at the upper end thereof in a neck portion 12 from which there extends a frustoconical portion 13. FIGS. 1, 3 and 4 of the drawings very clearly show, like the other details of the screw of the invention, this frustoconical portion 13.

The body 1 further includes a base column 14 of fairly low height. This base column 14 is provided with a facetted external surface. It is particularly useful for it to have a form similar to a nut, that is a hexagonal cross section, although for the desired purposes explained hereinafter, any other polygonal form may be useful, for example a square section.

The specific utility of the base column 14 having several flat surfaces 15 on the outside thereof, as seen in FIG. 4, is to allow the use of an appropriate tool or medical instrument in engagement in therewith so that the screw may be properly threaded when it is installed in the orifice made to receive it.

At the upper end of the main body 1 there is the axial bore 16 which, terminating in a blind bottom 17, has a relatively long length extending over approximately one half of the total length of the body 1. In said axial bore 16 there are two well differenciated portions: an initial portion 18 which is closer to the outside, and an end portion 19 which extends from portion 18 to the blind bottom 17. The initial portion 18 is provided with an internal thread 20 starting at the edge 21 of the outlet orifice 22 of the axial bore 16.

It should be pointed out that the diameter D of the upper circular edge 23 of the fustroconical portion 13 is clearly greater than the length of the larger diagonal DM of the polygonal form of the base column 14. For this reason, there is defined on the upper surface of the fustroconical portion 13 a narrow annular surface 24.

Also forming part of the screw for dental implants according to the invention, additionally, is a removable cap 25 the purpose of which is to screw on the base column 14 such as to cover it completely. This removable cap 25 is held in position on the base column 14, by way of a screw 26 passing through an appropriate orifice 27 in the end of the cap 25 and which screws into the upper axial bore 16, using the internal thread 20 of the initial portion 18. It may be seen in FIG. 3 how the cap fits completely on the base column 14, due to the fact that the circular edge 28 of the orifice 29 engages snugly against the said narrow annular surface 24.

The above described screw is used as follows:

After the main body 1 has been placed in its location in the maxillary bone, the upper portion extending outwardly is covered by the removable cap 25, held firmly in place by the screw 26.

On the elapse of the time that the medical treatment advises, the cap 25 is removed after removing the retaining screw 26, the upper axial bore 16 being available for receiving the threaded element, foreign to the structure of the screw, firmly holding the dental prosthesis as much. In certain cases, the same retaining screw 26 may be reused.

The constructive details of the screw of the embodiment may be as follows:

| | |
|---|---|
| Constituent material: | titanium |
| Weight (variable according to length): | 335 to 650 mg |
| External threaded portion | |
| Internal diameter: | 2.5 mm |
| External diameter: | 3 to 4.5 mm |
| Length (variable): | 6 to 16 mm |
| Tapered portion | |
| Lower diameter: | 3.5 mm |
| Upper diameter: | 4.5 mm |
| Length (fixed): | 3 mm |
| Hexagonal portion | |
| Internal thread diameter: | 1.4 to 1.6 mm |
| External diameter: | 3 mm |
| Length (fixed): | 2 mm |

I claim:

1. A screw for dental implants, comprising a single-piece main metallic body (1) having a tapered lower end (2-3) in which a central cavity (4) is formed, said cavity extending axially a relatively small depth into said body, said tapered lower end (2-3) merging into an elongated cylindrical portion (10) provided along the whole length thereof with an external screwthread (11), said cylindrical portion merging into a frustoconical portion (13), a connecting neck defined between said cylindrical portion and said frustoconical portion, the frustoconical portion (13) merging into a base column (14) of a low length and having a polygonal cross section, said base column forming an upper end of the screw body (1) and being provided with an axial bore (16) extending over approximately a half of the overall length of the screw, said axial bore including an initial portion (18) provided with an internal screwthread (20) which starts at an edge (21) of an outlet orifice (22) and extends over a major portion of the length of the initial portion, and a non-threaded end portion (19) terminating in a blind bottom (17) of the said axial bore (16).

2. A screw for dental implants according to claim 1, wherein a longer diagonal (DM) of the cross-section of the base column (14) is shorter than a diameter (D) of an upper annular edge (23) of the frustoconical portion (13) whereby a free annular surface (24) is formed at a transition where said frustoconical portion merges into said base column.

3. A screw for dental implants, according to claim 2, further comprising a removable cap (25) fitted on the base column (14) to integrally cover the same and a central retaining screw (26) which extends through a central bore (27) of the cap (25) and is screwed in the axial bore (16) of the body (1) to hold said cap on said body.

4. A screw for dental implants, according to claim 3, wherein the cap (25) engages a peripheral surface of the base column and has an edge (28) seated on said free annular surface (24).

5. A screw for dental implants, according to claim 1, wherein the central cavity (4) at an open end (2) thereof is provided with an outlet orifice (6) formed by a diametral transverse cut (8) forming two notches (9-9') in mutually opposite positions.

6. A screw for dental implants, according to claim 1, wherein said main body is made of titanium.

7. A screw for dental implants, according to claim 1, wherein said base column has a square cross-section.

8. A screw for dental implants, according to claim 1, wherein the base column has a hexagonal cross-section.

* * * * *